United States Patent
George et al.

(10) Patent No.: US 9,977,060 B2
(45) Date of Patent: May 22, 2018

(54) CHANNEL INTEGRITY DETECTION

(71) Applicant: CARDIOINSIGHT TECHNOLOGIES, INC., Independence, OH (US)

(72) Inventors: Brian P. George, Cleveland, OH (US); Charulatha Ramanathan, Solon, OH (US); Ping Jia, Solon, OH (US); Qingguo Zeng, Solon, OH (US); Venkatesh Vasudevan, Beachwood, OH (US); Maria Strom, Moreland Hills, OH (US); Ryan Bokan, Cleveland, OH (US); Rémi Dubois, Merignac (FR)

(73) Assignee: Cardioinsight Technologies, Inc., Independence, OH (US)

( * ) Notice: Subject to any disclaimer, the term of this patent is extended or adjusted under 35 U.S.C. 154(b) by 0 days. days.

(21) Appl. No.: 15/269,488

(22) Filed: Sep. 19, 2016

(65) Prior Publication Data

US 2017/0003332 A1     Jan. 5, 2017

Related U.S. Application Data

(63) Continuation of application No. 13/890,058, filed on May 8, 2013, now Pat. No. 9,470,728.
(Continued)

(51) Int. Cl.
   *G06F 19/00*     (2018.01)
   *G01R 25/00*     (2006.01)
(Continued)

(52) U.S. Cl.
   CPC ............ *G01R 25/00* (2013.01); *A61B 5/0035* (2013.01); *A61B 5/0402* (2013.01);
(Continued)

(58) Field of Classification Search
CPC .... A61B 5/04012; A61B 5/726; A61B 5/0476
(Continued)

(56) References Cited

U.S. PATENT DOCUMENTS

| 4,862,897 A | 9/1989 | Eisenberg et al. |
| 4,922,920 A | 5/1990 | Thie et al. |

(Continued)

FOREIGN PATENT DOCUMENTS

| JP | 3423324 B2 | 7/2003 |
| WO | 2004008373 | 1/2004 |

(Continued)

OTHER PUBLICATIONS

International PCT Application No. PCT/US2013/040184 Filed: May 8, 2013; International Search Report and Written Opinion; Authorized Officer: Tae Hoon Kim; Date of Actual Completion: Sep. 17, 2013; 9 pp.

(Continued)

*Primary Examiner* — Edward Raymond
(74) *Attorney, Agent, or Firm* — Tarolli, Sundheim, Covell & Tummino LLP

(57) ABSTRACT

A computer-implemented method can include determining an amplitude for each of a plurality of input channels, corresponding to respective nodes. A measure of similarity can be computed between the input channel of each node and the input channel of its neighboring nodes. The method can also include comparing an amplitude for each node relative to other nodes to determine temporary bad channels. For each of the temporary bad channels, a measure of similarity can be computed between the input channel of each node and the input channel of its neighboring nodes. Channel integrity can then be identified based on the computed measures of similarity.

22 Claims, 9 Drawing Sheets

Related U.S. Application Data

(60) Provisional application No. 61/644,746, filed on May 9, 2012.

(51) Int. Cl.

| | | |
|---|---|---|
| *A61B 5/00* | (2006.01) | |
| *A61B 5/0402* | (2006.01) | |
| *A61B 5/0408* | (2006.01) | |
| *A61B 5/0428* | (2006.01) | |
| *A61B 5/0452* | (2006.01) | |
| *A61B 6/00* | (2006.01) | |
| *A61B 8/08* | (2006.01) | |
| *A61B 5/0476* | (2006.01) | |
| *A61B 5/0488* | (2006.01) | |
| *A61B 5/0496* | (2006.01) | |

(52) U.S. Cl.
CPC ...... *A61B 5/04085* (2013.01); *A61B 5/04288* (2013.01); *A61B 5/04525* (2013.01); *A61B 5/7203* (2013.01); *A61B 5/7221* (2013.01); *A61B 5/7246* (2013.01); *A61B 5/7264* (2013.01); *A61B 5/0476* (2013.01); *A61B 5/0488* (2013.01); *A61B 5/0496* (2013.01); *A61B 6/5247* (2013.01); *A61B 8/5261* (2013.01)

(58) Field of Classification Search
USPC .......................................... 702/72, 182–185
See application file for complete search history.

(56) References Cited

U.S. PATENT DOCUMENTS

| | | |
|---|---|---|
| 4,974,598 A | 12/1990 | John |
| 4,979,110 A | 12/1990 | Albrecht et al. |
| 4,991,587 A | 2/1991 | Blakeley et al. |
| 4,993,421 A | 2/1991 | Thornton |
| 5,054,496 A | 10/1991 | Wen et al. |
| 5,161,539 A | 11/1992 | Evans et al. |
| 5,810,740 A | 9/1998 | Paisner |
| 6,263,235 B1 | 4/2001 | Kaiser et al. |
| 6,370,423 B1 | 4/2002 | Guerrero et al. |
| 6,397,845 B1 | 6/2002 | Burton |
| 2004/0059761 A1 | 3/2004 | Hively |
| 2006/0095083 A1 | 5/2006 | Zhang et al. |
| 2007/0232948 A1 | 10/2007 | Stadler et al. |
| 2008/0269813 A1 | 10/2008 | Greenhut et al. |
| 2010/0094155 A1 | 4/2010 | Prichep |
| 2011/0043217 A1 | 2/2011 | Tszampazis et al. |
| 2011/0282180 A1 | 11/2011 | Goldkuhl et al. |
| 2012/0242501 A1* | 9/2012 | Tran .................. A61B 5/0024 340/870.02 |

FOREIGN PATENT DOCUMENTS

| | | |
|---|---|---|
| WO | 2004034886 | 4/2004 |
| WO | 2007146864 | 12/2007 |
| WO | 2008034886 A1 | 3/2008 |

OTHER PUBLICATIONS

"Supplementary European Search Report"; European Application No. 13787069; International Filing Date: May 13, 2013; Date of Completion: Dec. 1, 2015; 12 pgs.

Koessler, L. et al.; "Spatial Localization of EEG Electrodes"; Neurophysiology Clinique—Clinical Neurophysiology, Elsevier, Paris, FR, vol. 3, No. 2, Apr. 1, 2007; pp. 97-102, XPO253201869, ISSN: 0987-7053, DOI: 10.1016/J.NEUCLI.2007.03.002 [Retrieved on Apr. 1, 2007].

Gronlund, C., et al.; "On-Line Signal Quality Estimation of Multichannel Surface Electromyograms"; Medical and Biological Engineering and Computing, Springer, Heildelberg, DE, vol. 43, No. 3, May 1, 2005; pp. 357-364, XP001508011; ISSN: 0140-0118, DOI: 10.1007/BF02345813.

Canadian Application No. 2873042, Filed May 8, 2013, Canadian Office Action dated Jan. 16, 2017, 5 pgs.

* cited by examiner

CHANNEL INTEGRITY DETECTION

CROSS-REFERENCE TO RELATED APPLICATION

This application is a continuation of U.S. application Ser. No. 13/890,058 filed May 8, 2013, and entitled CHANNEL INTEGRITY DETECTION which claims the benefit of U.S. Provisional Patent Application No. 61/644,746, filed May 9, 2012 and entitled Automatic Bad Channel Detection. Each of the above-identified applications is incorporated herein by reference in its entirety.

TECHNICAL FIELD

This disclosure relates to channel integrity detection.

BACKGROUND

In some examples, body surface electrical activity (e.g., ECG signals) can be sensed by an arrangement of electrodes. The sensed signals can be processed for a variety of applications, such as for body surface mapping or electrocardiographic mapping. Since these and other processing methods can depend on body surface potential data, the quality of data for each input channel can affect the quality of the output results based on signal processing. In some types of signal processing, the signal processing can be very sensitive to anomalies in the input channels. For instance, significant noise, such as line noise or large changes in amplitude, or other variations in the input channels could produce inaccurate results as well as overshadow the important physiological information. This could render the resulting outputs computed from such input channels non-diagnostic or uninterpretable.

SUMMARY

This disclosure relates to channel integrity detection, such as to mitigate undesirable effects of noisy input channels on further processing and analysis.

In one example, the channel integrity detection can be implemented as a non-transitory computer readable medium having instructions. The instructions can include a preprocessing stage to analyze input channel data for a plurality of input channels to detect channels having an integrity that is considered one of bad or good, each of the plurality of input channels corresponding to a respective one of a plurality of nodes. A first spatial similarity measurement function can compute a measure of similarity between the input channel data for each of the plurality of nodes and a set of neighboring nodes to identify a spatial correlated set of channels having an integrity that is considered one of bad or good. An amplitude analyzer function can determine a subset of channels meeting amplitude criteria. A second spatial similarity measurement function can compute, for each channel in the subset of channels meeting the amplitude criteria, a measure of similarity between the input channel data for each node and a set of neighboring nodes to identify an amplitude correlated set of channels having an integrity that is considered one of bad or good. A combiner can store output data representing the integrity of plurality of input channels based on the channels detected by the preprocessing stage, the channels identified by the spatial correlated set of channels and the channels identified by the amplitude correlated set of channels.

In another example, a computer-implemented method can include determining an amplitude for each of a plurality of input channels, corresponding to respective nodes. A measure of similarity can be computed between the input channel of each node and the input channel of its neighboring nodes. The method can also include comparing an amplitude for each node relative to other nodes to determine temporary bad channels. For each of the temporary bad channels, a measure of similarity can be computed between the input channel of each node and the input channel of its neighboring nodes. Channel integrity can then be identified based on the computed measures of similarity.

DETAILED DESCRIPTION

Figure 1:
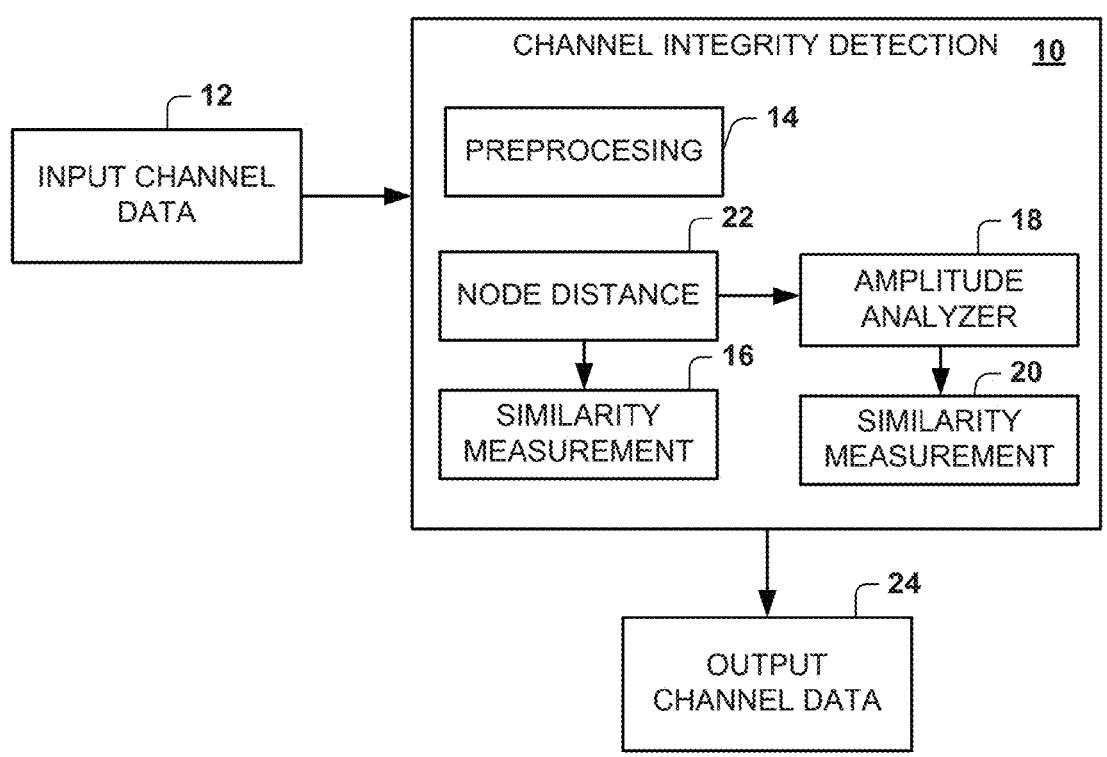
FIG. 1 depicts an example of a channel integrity detection system.

This disclosure relates to an apparatus, system or method that can determine channel integrity for a plurality of input channels. Each of the input channels can carry sensed electrical signals, such as electrophysiological signals from a patient. The sensed electrical signals for the respective channels can provide input channel data. In some examples, the approach disclosed herein can detect channels that may be detrimental to further signal processing sensitive to anomalous signals, such as line noise, large changes in amplitude or other variations in the input channels. The channel integrity detection disclosed herein thus enables detection and removal of channels determined to adversely affect such computations. In some examples, the detection and removal can be fully automated or semi-automated.

The channel integrity detection can perform pre-processing on the input channel data to identify certain types of faults or invalid channels, such as can include detecting disconnected sensing electrodes (e.g., saturated input channels), or other amplitude ranges (e.g., low and high amplitude ranges) that might adversely affect the signal processing. Additionally processing can be performed to compute a measure of spatial similarity (e.g., correlation) between the signals for a given node and its respective neighboring nodes. Signal channels having a low spatial correlation or otherwise uncorrelated relative to their respective neighbors can be identified as low integrity channels (e.g., also referred to herein as "bad channels"), and thus can be removed from further signal processing and analysis. Additional amplitude analysis can be performed for additional channel integrity detection. The amplitude analysis can be performed to identify outlier channels meeting certain amplitude conditions, on which additional similarity measurements can be performed to identify a further subset of channels that may have low channel integrity. Each of the identified low integrity channels, based on the preprocessing, the spatial similarity measurement and the amplitude analysis, can be combined to create a list of bad channels. The identified bad channels can be removed from further processing and signal analysis, such as to provide input channel data that includes the higher integrity channels.

As an example, the further processing and analysis can include reconstructing signals on a body surface based upon the input channel data (e.g., via an inverse solution). Additional calculations can be performed on the reconstructed data, such as to generate one or more graphical maps and characterize the reconstructed data. By removing such outlier channels from further processing, the approach can not only achieve improved accuracy in such further processing and analysis but also improves the system's workflow, such as by reducing preprocessing time.

Additionally, in some examples where a significant portion of the channels have been identified as "bad channels", a graphical map can be generated to identify the area of low resolution on a surface structure so that a user can determine if the affected area resides within a region of interest. A user can in turn select to continue in view of the identified low resolution area or make additional adjustments with respect to the sensing nodes that have been identified as "bad channels". A graphical user interface can also be provided to allow a user to selectively include or exclude one or more input channels from the analysis such as may be used to manually override the automatic removal of the identified bad channels.

FIG. 1 depicts an example of a channel integrity detection system 10 that can be utilized to provide an indication of channel integrity for a plurality of input channels. The channel integrity system 10 can be implemented as hardware, software (e.g., a non-transitory medium having machine readable instructions) or a combination of hardware and software. Signal information associated with each of the plurality of input channels can be provided by input channel data 12. The input channel data 12 can correspond to a digital representation of the sensed analog signals, such as electrophysiology information. In some examples, the input channel data 12 can be provided by sensing electrodes that are placed on a body surface of the patient, which can be an internal body surface (e.g., invasive) or an external body surface (e.g., non-invasive) or a combination thereof.

By way of example, the input channel data 12 can represent signals acquired (e.g., in real time or previously) from a plurality of body surface electrodes that are distributed across a patient's body, such as the thorax. The electrodes can be distributed evenly across the entire thorax, for example. In other examples, the electrodes can be distributed across a selected surface area (e.g., a sensing zone), such as corresponding to electrodes that are configured to detect electrical signals corresponding to a predetermined region of interest. In some examples, the input channel data 12 can correspond to filtered input data, such as based on line filtering and other signal processing (e.g., offset correction, analog-to-digital conversion and the like) to remove selected noise components from the input signals of the respective channels.

The channel integrity detection system 10 can include preprocessing 14, such as can include one or more method or function programmed to analyze the input channel data to identify certain types of outlier channels. In some examples, the preprocessing 14 can involve analysis of each channel without consideration of its neighboring channels. As used herein, the concept of neighbors, such a when referring to neighboring channels or nodes, refers to the spatial proximity of sensing electrodes or nodes that detect the input signals used to provide the input channel data 12. Thus, the preprocessing 14 can relate to analysis of the input channel data for each channel by itself.

As a further example, the preprocessing 14 can include detecting disconnected channels, such as based on detecting the voltage or current on the respective channels that can identify the channel and its sensor as being disconnected or non-operational. The preprocessing 14 can also include detecting low amplitude signals that may have an amplitude below a predetermined low voltage threshold. The preprocessing 14 can also include evaluation of high amplitude signals, such as within a predetermined range or exceeding a high amplitude threshold. Each of the ranges and user threshold associated with the preprocessing can correspond to default values or can be user programmable, such as in response to a user input.

A similarity measurement function 16 can be programmed to compute a measure of similarity between input signals, based on the input channel data 12, for each of the plurality nodes relative to a set of its local neighboring nodes. Each node's neighbors nodes can be determined from node geometry information, demonstrated in this example as node distance 22. For example, the set of neighboring nodes for a given node can include a first adjacent set of neighboring nodes surrounding the given node. The similarity measurement function 16 can thus identify channel integrity for a spatially correlated set of channels. The set of channels and their integrity can correspond to good channels or bad channels or otherwise provide an identifier to distinguish between good and bad channels based on the spatial similarity measurement. In some examples, the similarity measurement function can determine if any channels are low correlated or uncorrelated channels and, based on such determination, identify a set of low integrity channels.

An amplitude analyzer 18 can evaluate the amplitude of each of the respective channels. Like the similarity measurement function 16, the amplitude analyzer 18 can be performed on a set of channels excluding those that have been identified as low integrity channels by the preprocessing 14. The amplitude analyzer 18 can determine a subset of higher amplitude outlier channels based on a comparison of channel amplitudes for at least a substantial portion of the other nodes. For example, the amplitude analyzer 18 can determine which node or nodes (if any) have an amplitude greater than a statistically significant amplitude value derived from evaluation of amplitudes for all relevant channels (e.g., one or more standard deviations from the mean amplitude). The resulting subset of statistically high amplitude channels identified by the analyzer 18 thus can be further processed by similarity measurement function 20 to compute a measure of similarity (e.g., a correlation) between the input channel data 12 for each node of the subset and its local neighboring nodes. Since if the high amplitude channels might be determined to be good channels if they correlate well with the other neighboring channels, they can be considered temporary bad channels in this analysis. The similarity measurement function 20 can identify which statistically high amplitude channels exhibit a low correlation relative to its neighbors and thus can be considered bad channels. Alternatively or additionally, the similarity measurement function 20 can identify which channels are high integrity channels.

In some examples, the amplitude analyzer 18 and the similarity measurement functions 16 and 20 can employ node distance 22 to determine neighboring nodes for each of the nodes being analyzed. Additionally, the inter-node distance can be used to further constrain the similarity measurement functions 16 and 20. For example, if the node distance exceeds a predetermined distance, which can be a fixed value or be user programmable, such node can be excluded from analysis as neighboring node even if it is an actual spatial neighboring node. That is, the node distance 22 can constrain the measure of similarities to a spatial significant set of one or more nodes for each node that is processed by the amplitude analyzer 18 and the similarity measurement functions 16 and 20.

The channel integrity detection system 10 can provide output channel data 24 to identify a set of one or more nodes having low integrity such that it should be excluded from subsequent analysis. The output channel data 24 can be provided in terms of a list of nodes indexed according to input channel that can be provided to subsequent processing blocks so that the corresponding data for a given channel is not utilized in subsequent signal processing and data analysis. As disclosed herein, the output channel data can be provided in terms of channel integrity that is considered bad, good, or can identify both bad and good channels. In some examples, a logic value (e.g., 0 or 1) can be used to specify if a channel is good or bad. In other examples, an integrity value can be calculated to provide range of values representing the integrity of each channel, such that the degree of goodness or badness can be characterized by the output channel data. In an ideal situation, there would be no bad channels and the input channel data 12 for all channels would be utilized for further processing and analysis. In practice, however, the channel integrity detection system 10 can identify low integrity channels that can be removed from further processing and analysis as to improve the results.

Figure 2:
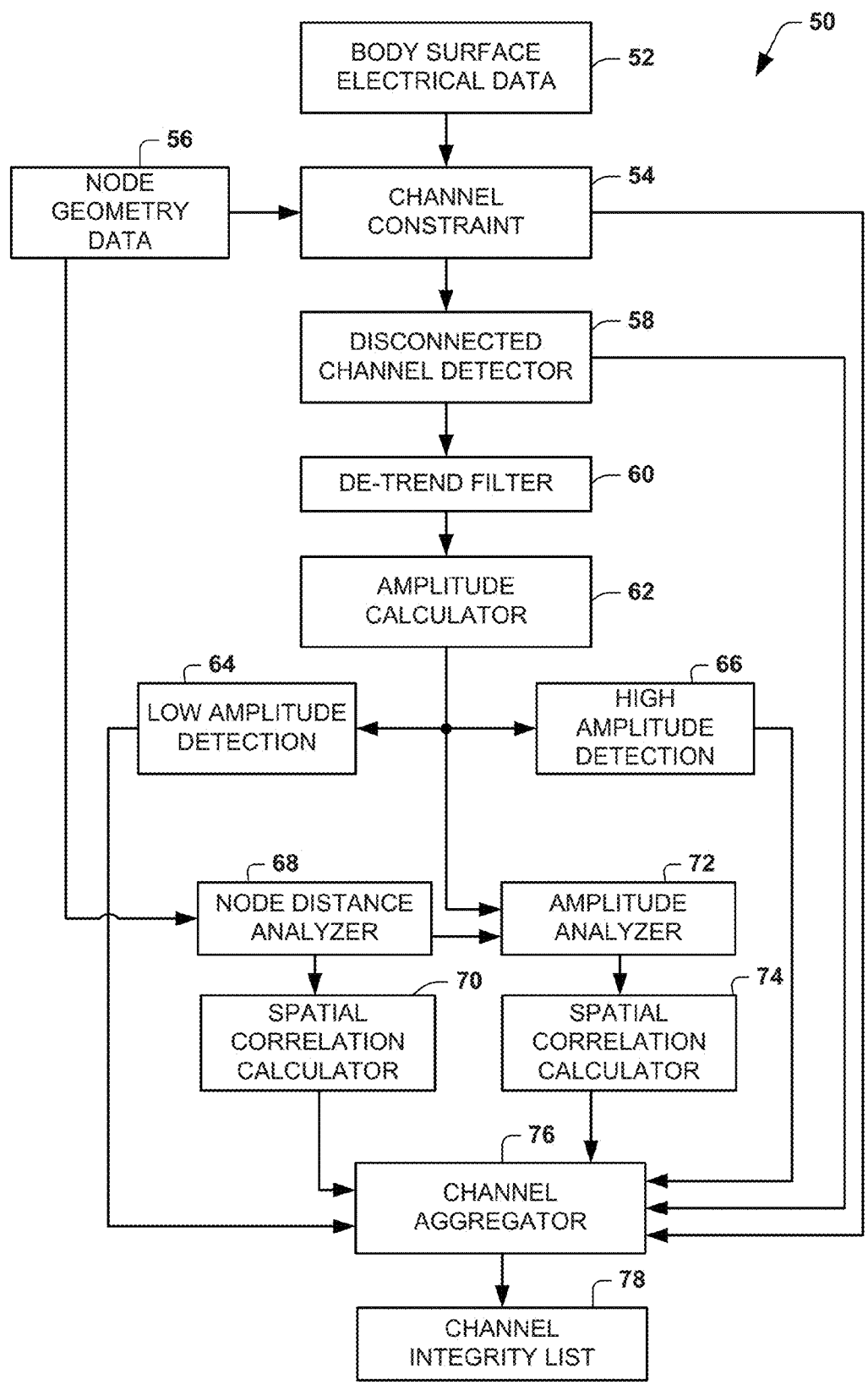
FIG. 2 depicts another example of a channel integrity detection system.

FIG. 2 depicts an example of a channel integrity detection system 50. In the example of FIG. 2, the channel integrity detection system 50 is demonstrated in the context of body surface electrical measurements that are represented by body surface electrical data 52 acquired for a respective patient over one or more time intervals. The body surface electrical data 52, for example, can include measured electrical signals (e.g., surface potentials) obtained from a plurality of sensing electrodes distributed across the body surface of a patient. Similar to other examples disclosed herein, the distribution of electrodes can cover substantially the entire thorax of a patient or the sensing electrodes can be distributed across a predetermined section of the body surface such as configured for detecting electrical signals predetermined as being sufficient to detect electrical information corresponding to a predetermined region of interest for the patient's body. In other For example, a set of electrodes can be preconfigured to cover a selected region of the patient's torso for monitoring atrial electrical activity of one or both atrium of a patient's heart, such as for studying atrial fibrillation. In other examples other preconfigured sets of electrodes can be utilized according to application requirements, which can include invasive and non-invasive measurements.

The body surface electrical data 52 can be stored in memory of a computer. The body surface electrical data can represent real time information that is streaming in from sensing electrodes as data is acquired from a patient's body or it can be stored from a previous study. Regardless of the temporal nature of the electrical data 52, the channel integrity detection system can improve accuracy of its further processing and analysis. Additionally, while the example of FIG. 2 is described in the context of channel detection for body surface electrical data, it is to be understood that the channel integrity detection, as disclosed herein, is equally applicable to other types of electrical signals including other types of electrophysiological signals (e.g., electromyography, electroencephalography, electrooculography, audiology and the like) as well as non-physiological electrical signals that may be monitored in a variety of other contexts.

An initial channel constraint 54 can be applied to the body surface electrical data 52. The channel constraint 54, for example can provide an index map that can be applied to the body surface electrical data to identify and remove channels that have been determined to be missing. For example, one or more electrodes can be physically removed from the sensing vest such that the information obtained by the channel is not relevant to the subsequent processing and analysis.

In another example where the body surface electrical data is to be mapped via inverse reconstruction to an anatomic envelope different from where the sensing has occurred, node geometry data 56 can be acquired for the sensing nodes. The node geometry data, for example, can identify the location of the sensing nodes (corresponding to sensing electrodes) in a respective correlated system. For example the node geometry data 56 can include a list of nodes, and neighbors for each node, such as can be produced by segmenting imaging data that has been acquired by an appropriate imaging modality. Examples of imaging modalities include ultrasound, computed tomography (CT), 3D Rotational angiography (3DRA), magnetic resonance imaging (MRI), x-ray, positron emission tomography (PET), fluoroscopy, and the like. Such imaging can be performed separately (e.g., before or after the measurements) utilized to generate the electrical data 52. Alternatively, imaging may be performed concurrently with recording the electrical activity that is utilized to generate the patient electrical data 14. The node geometry data 56 can also include coordinates (e.g., in three-dimensional space) for each of the nodes. Distances can be computed for neighboring nodes based on the coordinates (e.g., according to a distance metric, such as Euclidean distance). This can be stored in the node geometry data or it can be computed from such information by the system 50. In other examples, the node geometry data 56 can be acquired by manual measurements between sensing nodes or other means (e.g., a digitizer).

The channel constraint 54 thus can be programmed to identify a given channel corresponding to a node that was not appropriately segmented (e.g., no location in 3-D space exists for the node). Thus missing channels and/or unsegmented channels can be flagged or otherwise removed from the body surface electrical data 52. The channel constrained data can then be provided by the channel constraint function 54 for further analysis.

A disconnected channel detector 58 thus can operate on the constrained body surface electrical data (from channel constraint function 54) to determine if any channels have been disconnected from the substrate, such as the patient's body from which the measurements have been acquired. As an example, the disconnected channel detector 58 can be configured to detect saturation of an input channel such as by monitoring the value of the electrical signal. If the value of the electrical signal for a channel exceeds a threshold value (e.g., about + or −500 mV) or has a predetermined value (e.g., 0 V) for a plurality of consecutive samples, the corresponding channel can be determined to be disconnected. As an example, a measurement system (e.g., measurement system 110 of FIG. 3) to which the input channel signals are provided can be configured to saturate and obtain a predetermined value (e.g., about + or −500 mV) for a given channel if it loses contact with the body surface. In this way, the disconnected channel detector 58 can determine a saturated or disconnected channel which will be removed from further processing.

A de-trend filter 60 can be applied to the remaining body surface electrical data 52 (e.g., excluding bad channels that have been identified by the channel constraint 54 or the detector 58). The de-trend filter 60, for example, can be configured to remove the mean value or linear trend from each input channel (e.g., by FFT processing), which can remove baseline drift or other trending offsets from each respective channel. Such de-trending facilitates subsequent processing, including calculation of amplitude values for every signal channel. Additionally, by applying the de-trend filter 60 on the data provided by the disconnected channel detector 58 instead of before operation of the disconnected channel detector, the detection of saturated and disconnected channels is facilitated.

An amplitude calculator 62 is configured to compute a peak-to-peak amplitude on the de-trended input channel data for each of the channels. In the example where the body surface electrical data corresponds to electrocardiographic (ECG) data, the amplitude can be computed on de-trended ECG data. The computed amplitude values can be stored in memory with the body surface electrical data 52 associated with each of the channels. For example, the data 52 can be populated with an amplitude field according to the channel index with which the data is stored in memory.

A low amplitude detection function 64 can be programmed to determine if the calculated amplitude for each respective channel is below a predetermined low amplitude threshold. Each channel identified as a bad channel already (e.g., by channel constraint 54 and detector 58) can be excluded from the low amplitude detection function 64. For example the peak-to-peak amplitude of the signal for a given channel is less than the low voltage threshold, the given channels can be considered to be an extreme low amplitude and can be removed from further analysis (e.g., a bad or low integrity channel). The low amplitude threshold can be programmable or it can be set to a predetermined default value (e.g., about $1 \times 10^{-8}$ mV).

A high amplitude detection function 66 can be programmed to detect channels having an amplitude that is greater than a typical body surface electrical signal (e.g., greater than a typical ECG signal). The high amplitude detection function 66 thus can be programmed to compare the amplitude calculated (e.g., by amplitude calculator 62) for each channel relative to a high amplitude threshold. If the peak-to-peak amplitude of a given channel exceeds the high amplitude threshold, the channel can be identified in the electrical data 52 as a bad channel. The amplitude threshold can be programmable in response to user input or it can be set to a default value (e.g., about greater than 10 mV). The detection can be applied to each of the channels and the results stored in memory such as part of the body surface electrical data.

The system 50 can also include a node distance analyzer 68 that is programmed to quantify or characterize relative distance between the sensing nodes that are distributed across the body surface. For example, it has been determined that if the distance between neighboring nodes exceeds a certain distance, a comparison between neighboring channels may no longer be valid. As a result, the node distance analyzer 68 can programmed to determine if the distance between neighboring nodes exceeds distance threshold. The distance threshold can be a default value or it can be programmable to a desired value in response to a user input. The node distance analyzer 68 can analyze the nodes based on the node geometry data 56. As mentioned above, the node geometry data 56 can be obtained by a segmentation process performed on imaging data or other means.

The node distance analyzer 68 thus can be used to constrain spatially comparative processing, as disclosed herein, to include only those sensors and its neighbors that are within a prescribed proximity of each other. As a result, the likelihood of identifying a channel as a 'bad channel' can be reduced when a morphological change is due to distance between respective nodes instead of a spatial non-correlation between the respective input signals of such nodes.

An identification of the set of nodes and neighboring nodes that exceed the maximum node distance can be provided as an input to a spatial correlation calculator 70 and an amplitude analyzer 72. The spatial correlation calculator 70 can be programmed to calculate correlation coefficients between the input signals for each node not already excluded and its local neighboring nodes. The spatial correlation calculator 70 thus computes correlation coefficients from a cross correlation between a given central node and its local neighboring nodes, as constrained by the maximum node distance. The correlation coefficients between a central node and its neighboring nodes can be combined and compared relative to a correlation threshold (e.g., correlation cutoff value) to determine whether the signals are spatially non-correlated or uncorrelated. For example, the spatial correlation calculator 70 can be configured to compute a cross correlation between the central node and each of its neighbors that yields a coefficient value, and a mean correlation value can be computed for each node such as to provide a single correlation value for each node. The minimum mean correlation node can be removed from further analysis, including that to be performed by the amplitude analyzer 72 and following correlation analysis. The spatial correlation calculator 70 thus compares the correlation coefficients relative to the correlation threshold (e.g., a correlation cutoff value) and recalculates mean correlation values. The spatial correlation calculator 70 can repeat this process can continue until the minimum mean correlation value exceeds the correlation cut off value. If any channel had only one remaining neighbor for comparison, it can be not considered to not be a low integrity channel by the spatial correlation calculator 70.

The amplitude analyzer 72 is programmed to identify a proper subset of channels having a peak-to-peak amplitude greater than a statistically significant portion of the nodes. For example, the amplitude analyzer 72 can perform a histogram analysis of the peak-to-peak amplitude to detect outliers among each of the remaining channels (e.g., channels not already identified as bad channels). Those channels in the input data set provided to the amplitude analyzer that exceed the high amplitude threshold can be provided to a spatial correlation calculator 74. The high amplitude threshold can be determined from analysis of all the signal channels, such as based on an amount of variation (e.g., a percentage or a multiple of a standard deviation) greater than mean amplitude of the signals.

The spatial correlation calculator 74 can perform the same correlation as the spatial correlation calculation 70 or it can be different. For example, the spatial correlation calculator 74 can compute correlation coefficients based on performing a cross correlation between the signals for each respective node and its local set of neighboring nodes. As mentioned above, nodes exceeding the maximum node distance are not included in this analysis. Additionally, low amplitude channels and high amplitude channels as well as disconnected and channels otherwise constrained are also not included in the analysis performed by the spatial correlation calculator 74. As an example, the spatial correlation calculator 74 can require a larger amount of correlation than that required by the analysis implemented by the spatial correlation calculator 70 (e.g., the correlation threshold of calculator 70). That is the cross correlation performed by the spatial correlation calculator 74 can employ a more strict correlation threshold than that employed by the spatial correlation calculator 70.

A channel aggregator 76 can be configured to combine the list of bad channels detected by the analyzer components of the channel integrity detection system 50, such as including the channel constraint function 54, the disconnected channel detector 58, the low amplitude detection function 64, the high amplitude detection function 66, the spatial correlation calculator 70 and the spatial correlation calculator 74. The channel aggregator 76 in turn can provide a channel integrity list that can be utilized to exclude such channels from subsequent analysis. In other examples, the channel integrity list 78 represent good channels on which subsequent analysis is to be performed. In yet another example, the channel integrity list could provide an indication of both good channels and bad channels. In still another example, a channel integrity list could provide a quantified value representing a channel integrity for each of the respective nodes based upon the analysis performed by the channel integrity detection system 50. Regardless of the contents and type of information in the channel integrity list, the information can be stored in memory in conjunction with the body surface electrical data 52 for further processing and analysis.

By way of further example, other inputs to and the channel integrity detection system 50 can include variables demonstrated in the following table. As disclosed herein some of the variables can be set to default values or be user programmable. The outputs from the integrity detection system 50 can include variables representing a bad (and/or good) channel list. A list of saturated or disconnected channels can also be provided.

| Variable Name | Description |
|---|---|
| triangles | triangular mesh node connection list (part of the geometry data 56) |
| vertices | x, y, z coordinates of each node point (part of or determined from geometry data 56) |
| dataOrig | channel input data (electrical data 52) |
| ccCutOff | Correlation coefficient maximum value for bad channels (used by correlation calculator 70) |
| ampCutoffSDMultiplier | Amplitude standard deviation multiplier (used by amplitude analyzer 72) |

-continued

| Variable Name | Description |
|---|---|
| maxNodeDistValue | Maximum node distance (used by node distance analyzer 68) |
| badChannelZero | Previously detected bad channels - saturated (provided by channel constraint 54) |
| channelIndices | channel indices which references non missing channels |
| maxNodeDistMultiplier | Maximum node distance standard deviation multiplier (used by amplitude analyzer 72) |
| ccCutoffAmplitude | Amplitude correlation coefficient maximum value for bad channels (used by correlation calculator 74) |

Figure 3:
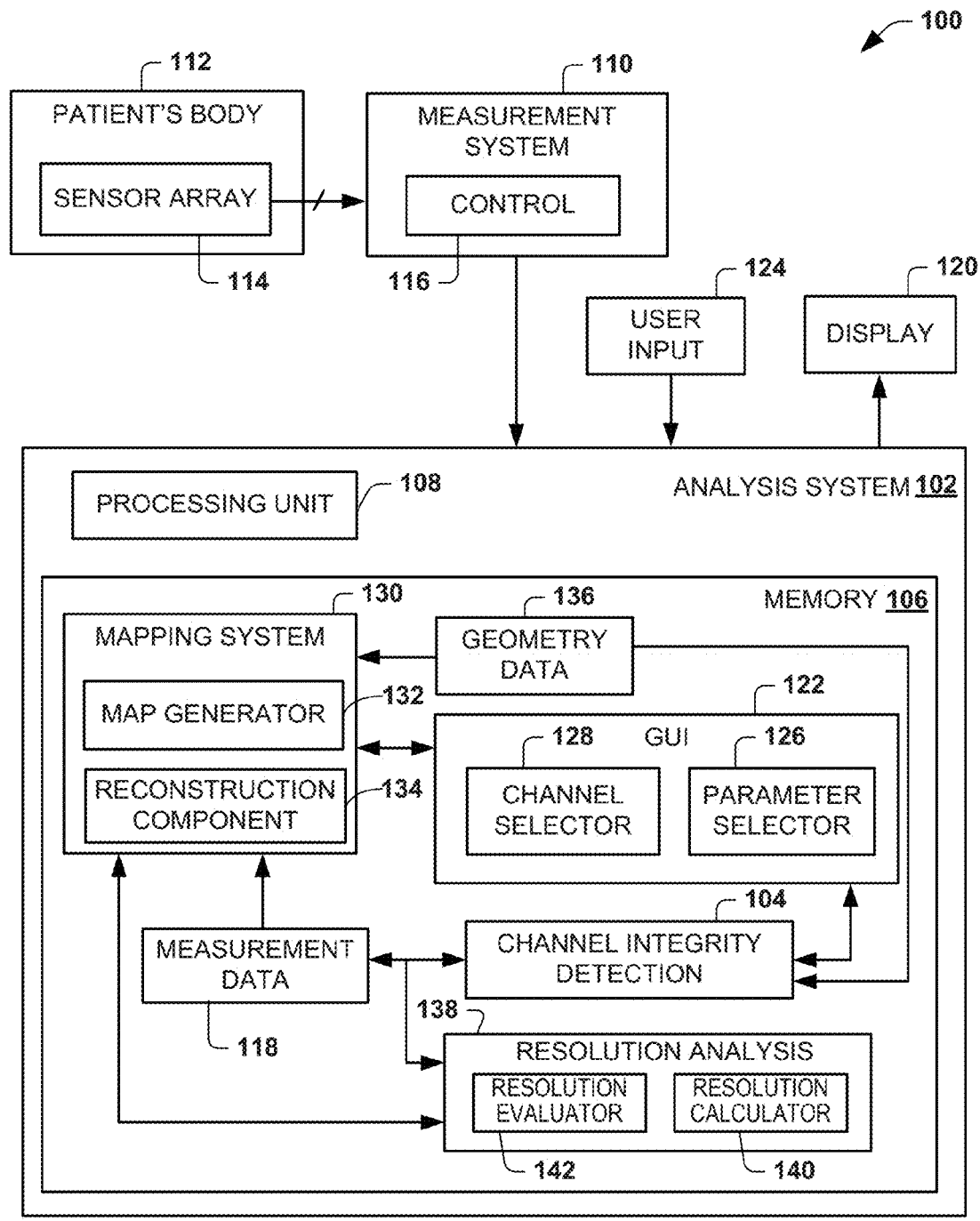
FIG. 3 depicts an example of an electrophysiological mapping system that can implement channel integrity detection.

FIG. 3 depicts an example of a system 100 that can be utilized for acquiring electrical activity sensed from a patient 108 and for analyzing the sensed electrical activity. In some examples, the sensed electrical activity can be used to generate one or more graphical representations (e.g., graphical maps of electroanatomic activity) based on the sensed electrical activity, such as for a region of patient anatomy. The system 100 can include an analysis system 102 that employs a channel integrity detection 104 as disclosed herein.

The analysis system 102 can be implemented as including a computer, such as a laptop computer, a desktop computer, a server, a tablet computer, a workstation or the like. The analysis system 102 can include memory 106 for storing data and machine-readable instructions. The memory 106 can be implemented, for example, as a non-transitory computer storage medium, such as volatile memory (e.g., random access memory), non-volatile memory (e.g., a hard disk drive, a solid-state drive, flash memory or the like) or a combination thereof.

The analysis system 102 can also include a processing unit 108 to access the memory 106 and execute the machine-readable instructions stored in the memory. The processing unit 108 could be implemented, for example, as one or more processor cores. In the present examples, although the components of the analysis system 102 are illustrated as being implemented on the same system, in other examples, the different components could be distributed across different systems and communicate, for example, over a network.

The system 100 can include a measurement system 110 to acquire electrophysiology information for a patient 112. In the example of FIG. 3, a sensor array 114 includes one or more electrodes that can be utilized for recording patient electrical activity. As one example, the sensor array 114 can correspond to an arrangement of body surface electrodes that are distributed over and around the patient's thorax for measuring electrical activity associated with the patient's heart (e.g., as part of an ECM procedure). In some examples, there can be about 200 or more sensors (e.g., about 252 sensors) in the array 114, each sensor corresponding to a node that defines a respective channel. An example of a non-invasive sensor array that can be used is shown and described in International application No. PCT/US2009/063803, which was filed 10 Nov. 2009, and is incorporated herein by reference. This non-invasive sensor array corresponds to one example of a full complement of sensors that can include one or more sensing zones. As another example, the sensor array 108 can include an application-specific arrangement of electrodes corresponding to a single sensing zone or multiple discrete sensing zones, such as disclosed in International application No. PCT/US2012/059957, which was filed 12 Oct. 2012, and is incorporated herein by reference. Additionally or alternatively, the sensor array 114 can include invasive sensors that can be inserted into the patient's body.

The measurement system 110 receives sensed electrical signals from the corresponding sensor array 108. The measurement system 110 can include appropriate controls and signal processing circuitry (e.g., filters and safety circuitry) for providing corresponding electrical measurement data 118 that describes electrical activity for each of a plurality of input channels detected by the sensors in the sensor array 114.

The measurement data 118 can be stored in the memory 106 as analog or digital information. Appropriate time stamps and channel identifiers can be utilized for indexing the respective measurement data 118 to facilitate the evaluation and analysis thereof. As an example, each of the sensors in the sensor array 114 can simultaneously sense body surface electrical activity and provide corresponding measurement data 118 for one or more user selected time intervals.

The analysis system 102 is configured to process the electrical measurement data 118 and to generate one or more outputs. The output can be stored in the memory 106 and provided to a display 120 or other type of output device. As disclosed herein, the type of output and information presented can vary depending on, for example, application requirements of the user.

As mentioned, the analysis system 102 is programmed to employ channel integrity detection methods 104 to improve the accuracy in processing and analysis performed by the analysis system. The channel integrity detection 104 can, for example, be implemented to perform any combination of the channel integrity detection functions and methods disclosed herein (see, e.g., FIGS. 1 and 2 and the corresponding description). The channel integrity detection 104 thus can compute an indication of which input channels are bad (or good) based on signal processing on the measurement data 118. The resulting channel integrity data provided by the detection methods 104 can be stored in the memory 106, such as in conjunction with the measurement data 118. In this way, bad channels can be removed automatically or selectively for further processing and analysis.

In some examples, the channel integrity detection 104 can interface with a graphical user interface (GUI) 122 stored as executable instructions in the memory 106. The GUI 122 thus can provide an interactive user interface, such that the thresholds and related parameters utilized by the channel integrity detection 104 can be set in response to a user input 124. The GUI 122 can provide data that can be rendered as interactive graphics on the display 120. For example, the GUI 122 can generate an interactive graphical representation that differentiates between good and bad channels (e.g., a graphical representation of the sensor array 114 differentiating graphically or otherwise between bad and good channels).

In the example of FIG. 3, the GUI includes a parameter selector 126 that can be employed to program channel integrity parameters (e.g., thresholds and constraints) implemented by the channel integrity detection 104. In some examples, default values can be utilized unless modified in response to a user input, such as disclosed herein.

The GUI 122 can also include a channel selector 128 programmed to select and deselect channels in response to a user input. The channel selector 128 can be employed to manually include or exclude selected channels. For instance, the GUI 122 can indicate (e.g., by graphical and/or textual indicators) on the display 120 which channels are missing channels to be excluded, a suggested set of channels that are to be excluded but can be editable via the GUI, and a set of channels considered to be high integrity (e.g., good) channels and are also editable via the GUI. A user can thus employ the channel selector 128 of the GUI 122 to include a bad channel that has been identified for removal or exclude a good channel that is identified for inclusion.

As a further example, the analysis system 102 can include a mapping system 130 that is programmed to generate electroanatomical map based on the measurement data 118, namely based on the measurement data for the channels determined to have a sufficient integrity (i.e., excluding bad channels). The mapping system 130 can include a map generator 132 that is programmed to generate map data representing a graphical (e.g., an electrical or electroanatomic map) based on the measurement data 118. The map generator 132 can generate the map data to visualize such map via the display 120 spatially superimposed on a graphical representation of an anatomical structure (e.g., the heart).

In some examples, the mapping system 130 includes a reconstruction component 134 programmed to reconstruct heart electrical activity by combining the measurement data 118 with geometry data 136 through an inverse calculation. The inverse calculation employs a transformation matrix and to reconstructs the electrical activity sensed by the sensor array 114 on the patient's body onto an anatomic envelope, such as an epicardial surface, an endocardial surface or other envelope. Examples of inverse algorithms that can be implemented by the reconstruction component 134 are disclosed in U.S. Pat. Nos. 7,983,743 and 6,772,004.

The reconstruction component 134, for example, computes coefficients for a transfer matrix to determine heart electrical activity on a cardiac envelope based on the body surface electrical activity represented by the electrical measurement data 118. Since the reconstruction onto the envelope can be sensitive to ingress and other noise on the respective input channels, the channel integrity detection 104 helps to remove data for channels that would likely adversely affect the process. Additionally, the reconstruction component 134 can utilize interpolated measurement data computed for the identified bad channels. Such interpolation for a given channel can be calculated based on signal values determined from its neighboring nodes, for example. The possible effect of such interpolation on the resolution provided in a graphical electroanatomic map can vary depending on the quantity and spatial distribution of bad channels, as disclosed herein.

The map generator 132 can employ the reconstructed electrical data computed via the inverse method to produce corresponding map of electrical activity. The map can represent electrical activity of the patient's heart on the display 120, such as corresponding to a map of reconstructed electrograms (e.g., a potential map). Alternatively or additionally, an analysis system 102 can compute other electrical characteristics from the reconstructed electrograms, such as an activation map, a repolarization map, a propagation map or other electrical characteristic that can be computed from the measurement data. The type of map can be set in response to the user input 124 via the GUI 122.

By way of further example, the patient geometry data 136 can be acquired using nearly any imaging modality (e.g., x-ray, computed tomography, magnetic resonance imaging, ultrasound or the like) based on which a corresponding representation can be constructed, such as described herein. Such imaging may be performed concurrently with recording the electrical activity that is utilized to generate the measurement data 118 or the imaging can be performed separately. As another example, the geometry data 136 can correspond to a mathematical model of a torso that has been constructed based on image data for the patient's organ. A generic model can also be utilized to provide the geometry data 136. The generic model further may be customized (e.g., deformed) for a given patient, such as based on patient characteristics include size image data, health conditions or the like. Appropriate anatomical or other landmarks, including locations for the electrodes in the sensor array 108 can also be represented in the geometry data 116, such as by performing segmentation of the imaging data. The identification of such landmarks can be done manually (e.g., by a person via image editing software) or automatically (e.g., via image processing techniques).

The analysis system 102 can also include a resolution analysis function 138 to determine the impact on resolution of analysis performed by the mapping system 130 based on the identified bad channels. As an example, the resolution analysis function 138 can include a resolution calculator 140 programmed to compute resolution for data that is reconstructed onto a prescribed surface (e.g., by the reconstruction component). As mentioned, the surface can include a surface envelope such as can include an anatomical surface, a surface of a model or a combination of a model and anatomical structure onto which electrical data is to be reconstructed, as represented by the geometry data 136. In some examples, the surface can include an epicardial surface or an endocardial surface of a patient's heart, and further may include an entire surface or a selected region of interest.

A resolution evaluator 142 can analyze the computed resolution over the surface, such as by comparing the computed resolution relative to a threshold. The threshold can be utilized to determine an area of low resolution that would be adversely affected by the identified bad channels. The area of low resolution, for example, can be provided to the map generator 132 and, in turn, be utilized to construct a graphical map that can be graphically presented to a user on the display 120. The user further can be provided an opportunity to select to continue or make other adjustments to the sensor array 114 in an effort to improve the channel integrity. In other examples, a user can select to proceed with analysis with the understanding that certain areas of the reconstructed data may occupy areas of low resolution and thus could contain associated inaccuracies. Such inaccuracies, however, may be insignificant when a desired region of interest resides outside the area of low resolution.

Figure 4:
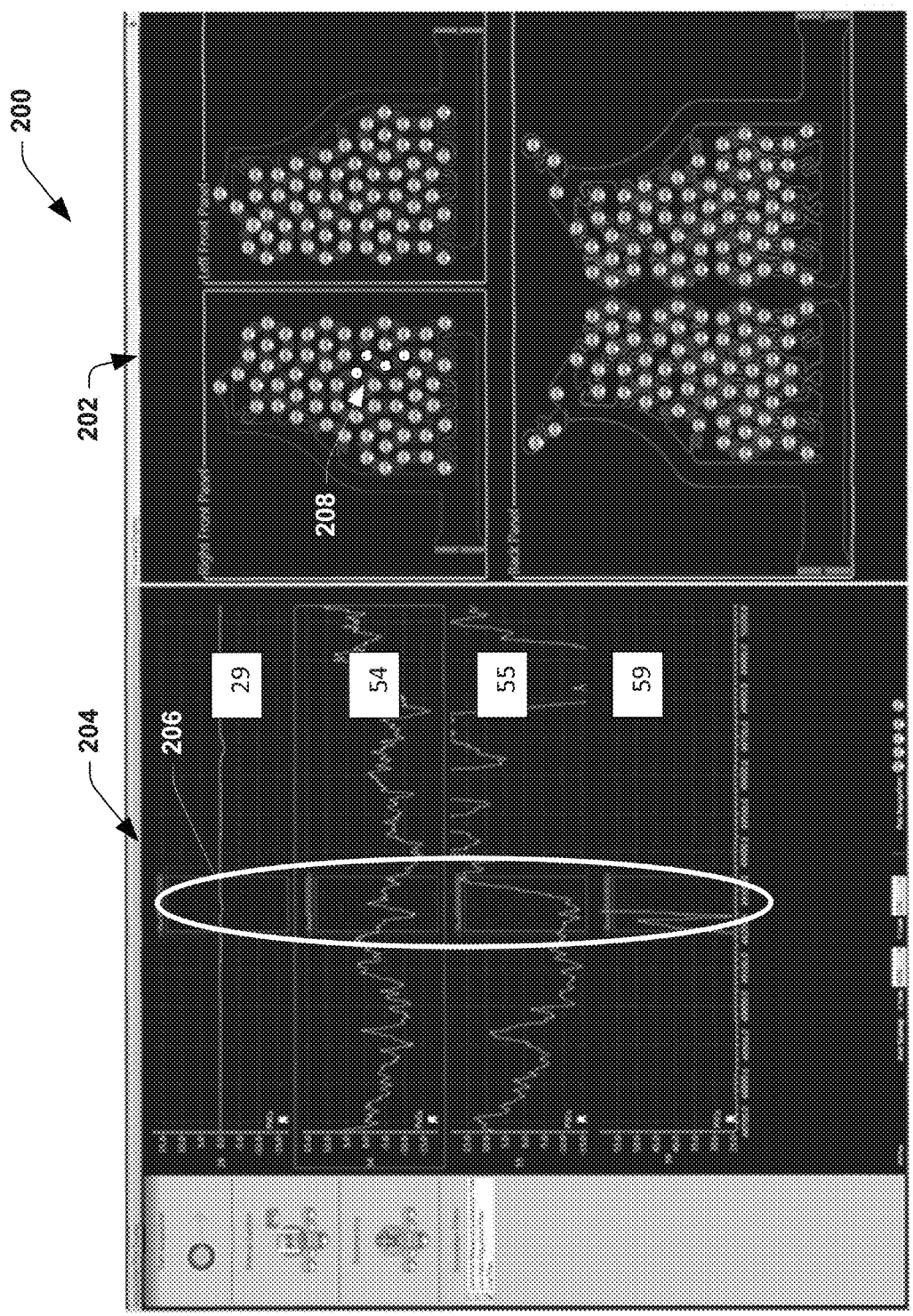
FIG. 4 depicts an example of a graphical user interface demonstrating examples of high amplitude signals that can be identified via channel integrity detection.

FIG. 4 depicts an example of a GUI 200 that includes a first display portion 202 that includes a graphical depiction of a sensor array illustrates sensing nodes. Another portion of the GUI 200 includes a display portion 204 representing a set of electrical signals 206. The GUI 200 can correspond to the GUI 122 of FIG. 3, for example. The electrical signals 206 demonstrated in FIG. 4 include signals for a selected set of channels 208 identified as channels 29, 54, 55 and 59 of the set of channels. The peak-to-peak amplitude of the channel 54 is approximately 13 mV. The peak-to-peak amplitude of the third channel 55 is approximately 30 mV. The first channel has an approximate peak-to-peak amplitude of about 30 mV. Each of the channels 54, 55 and 59 are examples of high amplitude channels that would be detected by the high amplitude detection function of the channel integrity detection method as disclosed herein.

Figure 5:
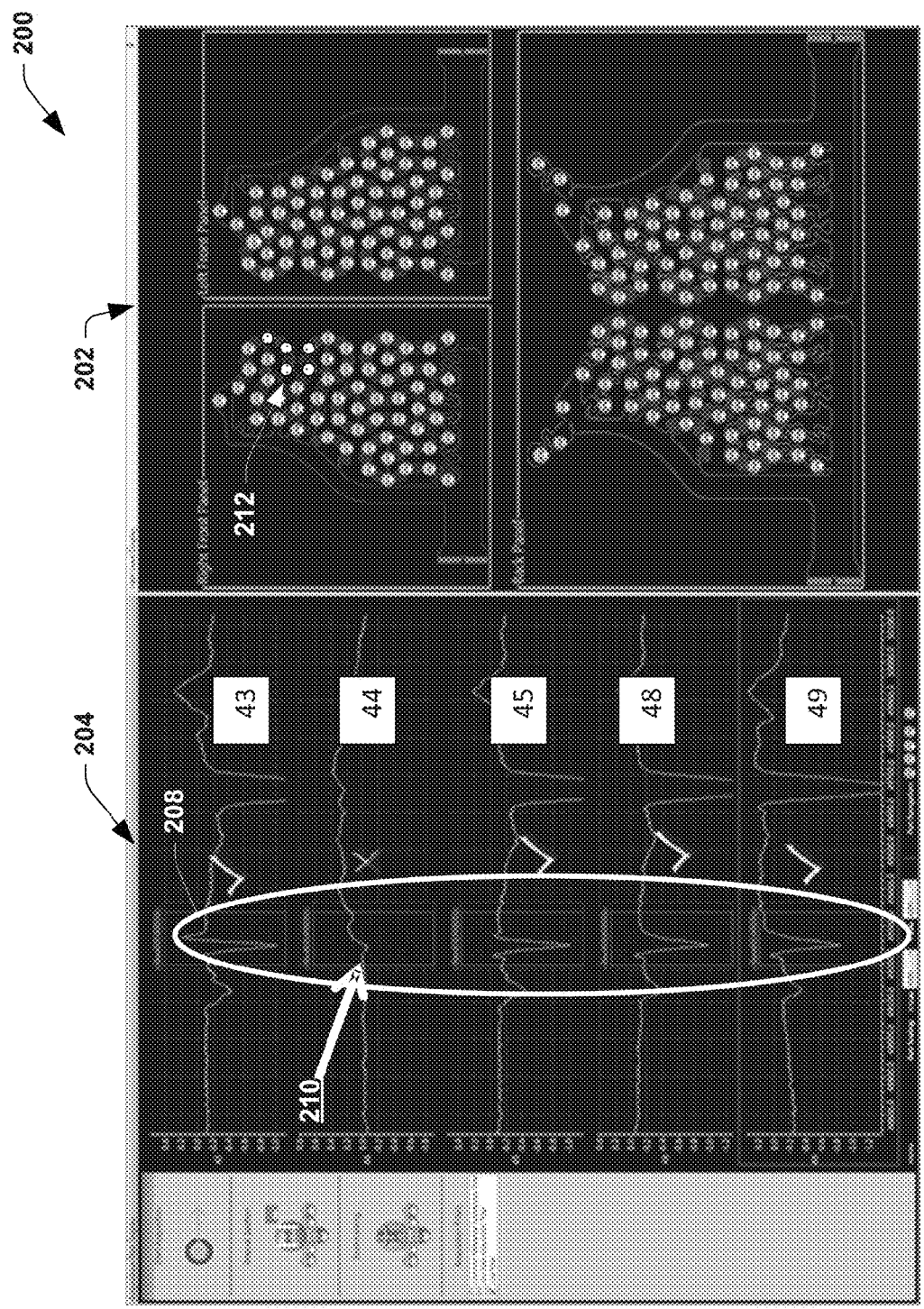
FIG. 5 depicts an example of another graphical user interface demonstrating examples of low spatially correlated signals that can be identified via channel integrity detection.

FIG. 5 depicts an example of the GUI 200 from FIG. 4 demonstrating signals 210 for a different selected set of channels 43, 44, 45, 48 and 49, demonstrated at 212. Based on the spatial measurement functions disclosed herein, it can be determined that each of the channels 43, 44, 45, 48, and 49 exhibits similar morphology, and thus would be spatially well correlated. However, the signal for channel 44 has a morphology not similar to its respective neighboring channels, and thus can be computed by the channel integrity detection method as a low integrity or bad channel.

Figure 6:
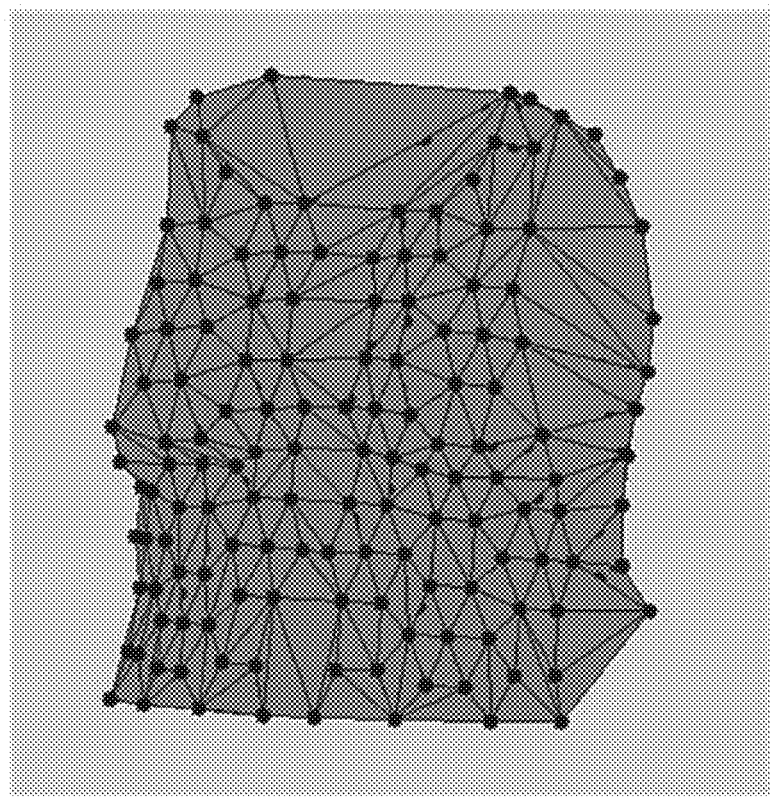
FIG. 6 depicts a graphical representation of sensing nodes that can be distributed across a patient's body surface.
Figure 7:
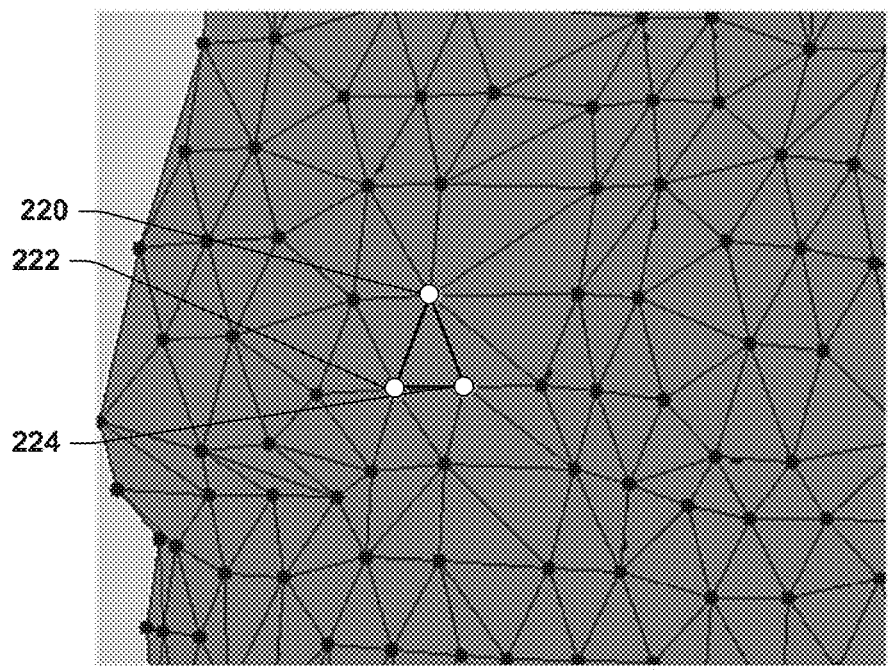
FIG. 7 depicts an enlarged view of a part of the nodes of FIG. 6 demonstrating a mesh configuration.

As an example, body surface electrophysiological channels are related spatially by the connections formed between each sensing node and its corresponding surrounding nodes. As shown in the example of FIGS. 6 and 7, the spatial relationship between nodes can be represented by a triangular mesh.

As a further example, geometry data (e.g., data 56 of FIG. 2 and data 136 of FIG. 3) for a segmented image set for a patient while a sensor array of electrodes is positioned on the patient body can provide data representing each node's spatial location (e.g., an x, y, z coordinate position). The geometry data can also provide a corresponding triangular mesh connection (e.g., node number triplets for the formation of each mesh triangle) for each node. For example, in FIG. 7, the nodes 220, 222, and 224 (highlighted) were connected by a corresponding triangulation triplet. The triangular connections across the body surface form a triangular mesh which can be used to provide the body surface information for subsequent processing, such as for inverse problem calculations, as disclosed herein.

Figure 8A:
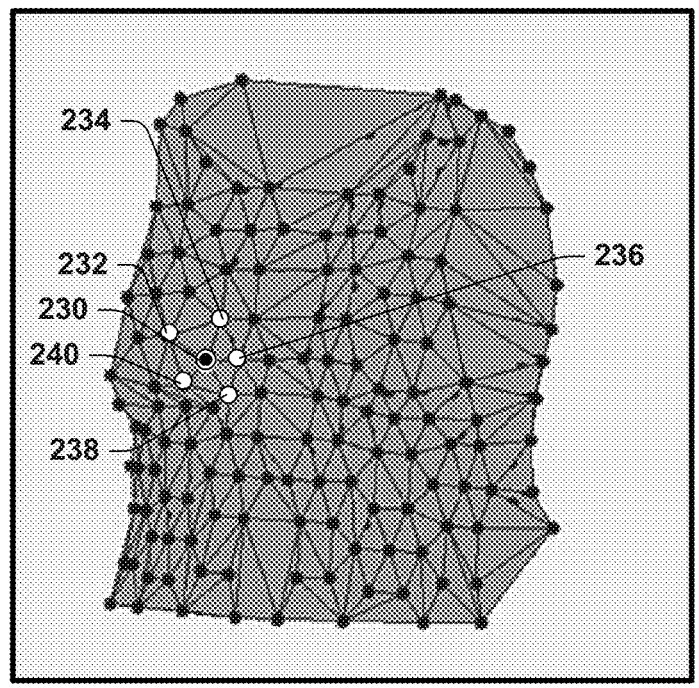
FIG. 8A depicts a representation of a node mesh structure demonstrating a central node surrounded by a set of local neighboring nodes.
Figure 8B:
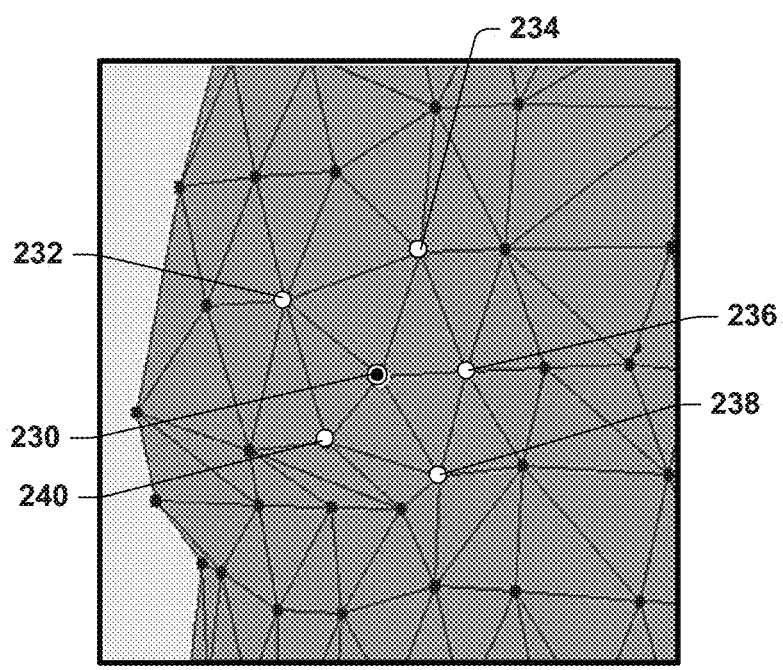
FIG. 8B is an enlarged view of part of the mesh structure of FIG. 8A further demonstrating the central node and its local neighboring nodes.

Each node point on the torso thus is connected by the triangular mesh to one or more neighboring node points. These surrounding nodes are considered the node's "neighbors". An example center node 230 and its local neighboring nodes 232, 234, 236, 238 and 240 are shown in FIGS. 8A and 8B. In one example of comparative calculations (e.g., by the similarity measurement 16, amplitude analyzer 18 and similarity measurement 20 of FIG. 1), the center node (e.g., node of interest) 230 is only compared relative to its adjacent neighboring nodes. In addition to the calculating the neighboring nodes, the node distances between each node and its specific neighbors are calculated (e.g., by the node distance function 22 of FIG. 1 or node distance analyzer 68 of FIG. 2). As disclosed herein, the node distances can be used to discriminate poor node comparisons based on distance. While this example includes only an immediately adjacent set of neighboring nodes 232, 234, 236, 238 and 240 as neighbors (e.g., which form a neighborhood of nodes), other degrees of proximity can be utilized in other examples. Additionally, the distance between each center node and its neighboring nodes can be utilized to provide a weighting applied to each correlation between the neighboring nodes. As a result, a more accurate correlation that varies as a function of distance can be utilized in the correlation between neighboring channels.

Figure 9:
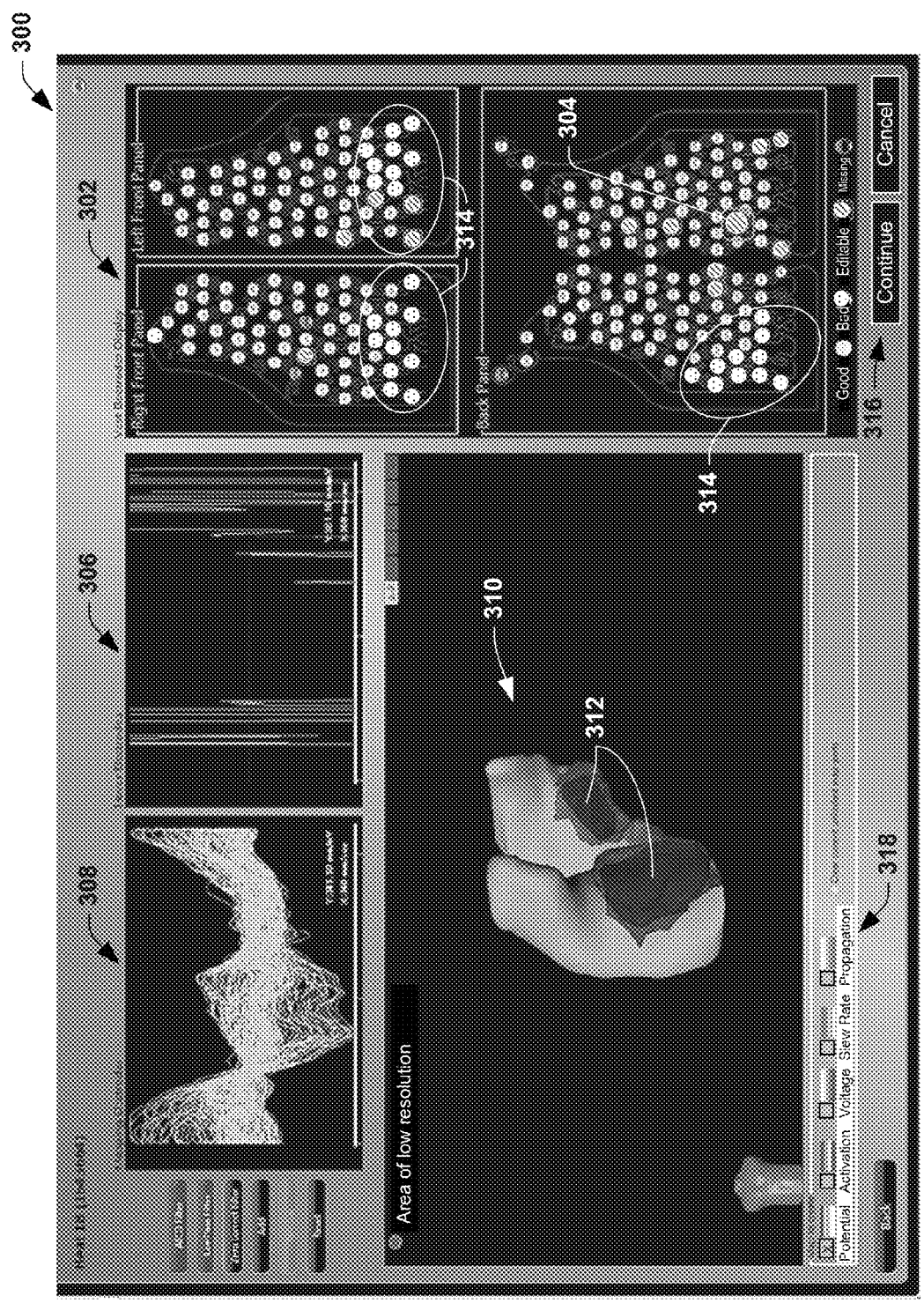
FIG. 9 depicts an example of a graphical user interface demonstrating additional signals that have been selected, a display of channel integrity as well as an example map that can be generated based on the signals detected by the sensing nodes.
Figure 10:
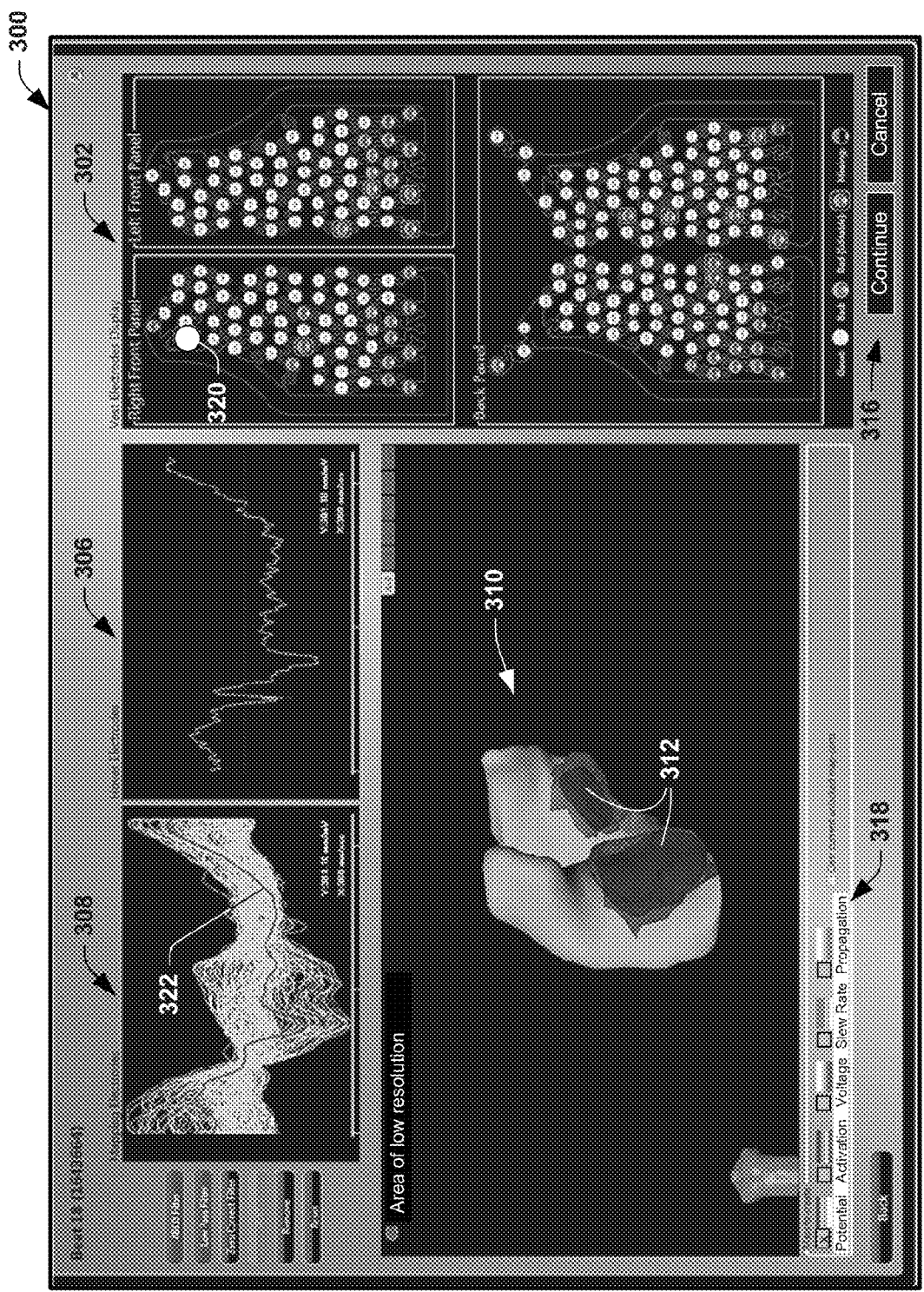
FIG. 10 depicts another example of a graphical user interface demonstrating examples of channel signals, sensing node integrity and a resulting map that can be generated based on the input signals detected by the sensing nodes.

FIGS. 9 and 10 demonstrate examples of a GUI 300, such as can correspond to the GUI 122 of FIG. 3. In the example of FIG. 9, the GUI 300 includes a plurality of display areas, at least some or all of which can include interactive GUI elements that can activate functions or methods in response to a user input. For example, an interactive electrode display area 302 includes a graphical representation of sensing nodes (e.g., electrodes of a sensor array), such as can correspond to electrodes distributed on a patient's body as disclosed herein. A scale is provided to inform the user of different levels of channel integrity, such as can include 'Good' channels, bad channels, bad but editable channels and missing channels. For example, the scale can utilize different colors, graphical indicia, text or any combination thereof to differentiate channel integrity that has been determined for each such channel, such as shown in FIG. 9. In this example one of the nodes 304 has been selected and its corresponding signal is presented in display area 306. Any number of one or more nodes can be selected to provide its signal in the display area 306. An adjacent display area 308 includes waveforms for each of the electrodes that have not been removed by the channel integrity detection or that has been removed (e.g., an editable channel) but has been reactivated by the user.

Also demonstrated in FIG. 9 is a graphical map 310. In this example, the graphical map 310 includes a graphical representation (e.g., via color coding) of one or more areas of low resolution, demonstrated at 312. The area of low resolution, for example, can be determined by a resolution analysis method (e.g., resolution analysis method 138 of FIG. 3) in conjunction with reconstruction of the sensed signals to a surface (e.g., the cardiac surface). Thus, the graphical map 310 can display the effect that the identified bad channels will have on the overall resolution of inverse calculations. In this example, the area of low resolution is the result of several bad channels, highlighted at 314, near the low edge of each panel of the array of electrodes. A user thus has an opportunity to cancel the process and adjust the sensing electrodes or the user can select to continue (e.g., via GUI elements 316) the process.

The GUI 300 also includes GUI elements 318 that can be utilized to select what type of map will be generated (e.g., by map generator 132 of FIG. 3) and presented in the map 310 in response to a user input. Examples of maps that can be created can include a potential map, an activation map, a voltage map, a slew rate map and a propagation map. Other maps could also be generated.

FIG. 10 depicts another example of the GUI 300 in which the same reference characters refer to the same parts introduced with respect to FIG. 9. In the example of FIG. 10, a given node 320 has been selected in response to a user input. The corresponding waveform is presented in the display area 306. The resulting mapped electrode following reconstruction for each of the good electrodes is demonstrated in display area 308. Additionally, since the selected node in this example has been determined (e.g., by channel integrity detection method 104 of FIG. 3) to be a good channel, its reconstructed waveform is highlighted (e.g., graphically differentiated) from the other reconstructed waveforms in the display area 308, as shown at 322. Similar to FIG. 9, the map 310 includes areas of low resolution 312 resulting from the impact of channels that have been determined to be bad channels (e.g., by channel integrity detection method 104 of FIG. 3).

In view of the foregoing, an automatic bad channel detection method has been disclosed to improve accuracy and user experience. The approach disclosed herein thus can enhance the user interaction and increase the ease of beat-by-beat analysis. The bad channel detection methods and systems can be implemented to identify and remove high amplitude and low spatially correlated signal channels. The remaining channels can be utilized to reconstruct electrical activity on a surface envelope (e.g., epicardial or endocardial electro grams) via potential-based inverse electrocardiography algorithms.

As will be appreciated by those skilled in the art, portions of the invention may be embodied as a method, data processing system, or computer program product. Accordingly, these portions of the present invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention are described herein with reference to flowchart illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims.

As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A system comprising:
   a plurality of electrodes to measure electrical signals corresponding to input channel data from a patient, each of the plurality of electrodes corresponding to a node that defines a respective input channel; and
   a processor to access memory comprising instructions executable by the processor, the instructions comprising:
   a first spatial similarity measurement function to compute a measure of similarity between the input channel data for each node and a set of neighboring nodes to identify a spatial correlated set of channels having an integrity that is considered one of bad or good;
   an amplitude analyzer programmed to determine a subset of channels meeting amplitude criteria;
   a second spatial similarity measurement function to compute, for each channel in the subset of channels meeting the amplitude criteria, a measure of similarity between the input channel data for each node and a set of neighboring nodes to identify an amplitude correlated set of channels having an integrity that is considered one of bad or good; and a combiner programmed to generate output data representing the integrity of the plurality of input channels based on the spatial correlated set of channels and the amplitude correlated set of channels; and a display device to provide a graphical representation of the output data that includes an indication of the integrity of the plurality of input channels, wherein the one or more channels with low integrity are selectively included or excluded from further processing according to a user input.

2. The system of claim 1, wherein the amplitude analyzer is further programmed to compare an amplitude value for each node relative to amplitude values for at least a substantial portion of the other nodes to determine temporary bad channels, which defines the subset of channels meeting the amplitude criteria.

3. The system of claim 2, wherein the second spatial similarity measurement function comprises a correlation calculator programmed to compute a cross correlation between the input channel data for each node, corresponding to the temporary bad channels, and the set of neighboring nodes.

4. The system of claim 2, wherein the instructions further comprise an amplitude calculator programmed to compute the amplitude values for each of the plurality of nodes based on the input channel data for each respective node, wherein the second spatial similarity measurement function comprises a correlation calculator programmed to compute a correlation coefficient value between the computed amplitude value of each of the temporary bad channels and its local neighboring nodes, the amplitude correlated set of channels being determined based on a comparison of the correlation coefficient value computed for each node relative to a threshold value.

5. The system of claim 1, wherein the first spatial similarity measurement function comprises a correlation calculator programmed to compute correlation coefficient values from a cross correlation computed between each of the plurality of nodes and its local neighboring nodes, the spatial correlated set of channels being determined based on a comparison of the correlation coefficient value for each node relative to a threshold value.

6. The system of claim 1, wherein the instructions further comprise a node distance analyzer programmed to compute distance between nodes based on locations of nodes determined from geometry data computed from image data that represents locations for the plurality of nodes, the geometry data being computed from image data, each set of neighboring nodes being determined based on the distance between nodes.

7. The system of claim 1, wherein the instructions further comprise a preprocessing stage programmed to analyze the input channel data to detect channels corresponding to the plurality of electrodes having an integrity that is considered one of bad or good, the combiner being programmed to generate output data representing the integrity of the plurality of input channels based on the integrity of the channels detected by the preprocessing stage, the spatial correlated set of channels and the amplitude correlated set of channels.

8. The system of claim 1, wherein the instructions further are programmed to automatically remove from the further processing each of the channels identified as having low channel integrity, the user input is to override or accept the automatic removal of channels from the further processing.

9. The system of claim 7, wherein the preprocessing stage further comprises a low amplitude detector programmed to identify each channel having an amplitude value that resides below a low amplitude threshold, the output data including channels identified by the low amplitude detector.

10. The system of claim 7, wherein the preprocessing stage further comprises a high amplitude detector programmed to identify each channel having an amplitude value that resides above a high amplitude threshold, the output data including channels identified by the high amplitude detector.

11. The system of claim 1, wherein the instructions further comprise:

a resolution calculator programmed to compute coefficients of a transformation matrix for at least a substantial portion of the plurality of input channels based on the data representing the integrity of the plurality of input channels; and an evaluator programmed to identify a low resolution spatial region based on an evaluation of the coefficients of the transformation matrix, a mapping generator programmed to generate a graphical map depicting the low resolution spatial region.

12. The system of claim 1, wherein the instructions further comprise a mapping system programmed to generate a reconstructed set of signals on an envelope based on the input channel data and the output data, such that an interpolated value is used for each bad channel that is excluded.

13. The system of claim 1, wherein the plurality of electrodes are one of positioned across a body surface of the patient or a surface of an internal anatomical structure of the patient.

14. The system of claim 13, wherein the internal anatomical structure is a heart.

15. A system comprising:

a sensor array comprising a plurality of electrodes to measure electrical activity across at least one of a body surface of a patient and a surface of an internal anatomical structure of the patient, each of the plurality of electrodes corresponding to a node that defines a respective input channel;

an analysis system to:
  determine an amplitude for each respective input channel;
  compute a measure of similarity between the input channel of each node and the input channel of its neighboring nodes;
  compare the amplitude for each node relative to other nodes to determine temporary bad channels;
  for each of the temporary bad channels, compute a measure of similarity between the input channel of each node and the input channel of its neighboring nodes;
  identify channel integrity for each respective input channel based on the computed measures of similarity; and
  store data associated with the identified channel integrity for each respective input channel in a memory; and a display to provide a graphical representation of the data associated with the identified channel integrity for each respective input channel, wherein the graphical representation illustrates one or more input channels with low integrity, wherein the one or more channels with low integrity are selectively included or excluded from further processing according to a user input.

16. The system of claim 15, wherein the analysis system is further to:
compute a resolution of reconstructed signals based on a plurality of input channels;
identify at least one region of low resolution resulting based on the computed resolution; and
generate a display of a graphical map representing the region of low resolution.

17. The system of claim 15, wherein the internal anatomical structure is a heart.

18. The system of claim 15, wherein the analysis system is further to automatically remove from the further processing each of the channels identified as having low channel integrity, the user input is to override or accept the automatic removal of channels from the further processing.

19. The system of claim 16, wherein the analysis system is further to generate the reconstructed signals using an inverse method based on the plurality of input channels, in which the identified bad channels are excluded from the generating and an interpolated channel value is used in place each identified bad channel.

20. The system of claim 15, wherein the analysis system is further programmed to determine a disconnected condition of a sensor for a given input channel to identify at least one bad channel.

21. The system of claim 15, wherein the measure of similarity computed for each of the temporary bad channels further comprises:
computing a correlation coefficient value between the computed amplitude value of each of the temporary bad channels and its neighboring nodes; and
comparing the correlation coefficient value computed for each node relative to a threshold value.

22. The system of claim 21, wherein the threshold value is a first threshold value and wherein the measure of similarity computed for each of the input channels further comprises:
computing a correlation coefficient value between the computed amplitude value of each of the temporary bad channels and its neighboring nodes; and
comparing the correlation coefficient value computed for each node relative to a second threshold value.

* * * * *